US009255907B2

(12) United States Patent
Heanue et al.

(10) Patent No.: US 9,255,907 B2
(45) Date of Patent: Feb. 9, 2016

(54) IDENTIFICATION OF SURGICAL SMOKE

(71) Applicant: Empire Technology Development LLC, Wilmington, DE (US)

(72) Inventors: Joseph Anthony Heanue, Oakland, CA (US); Tobias Funk, Martinez, CA (US); Kate LeeAnn Bechtel, Pleasant Hill, CA (US); Amish Parashar, Campbell, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 14/363,049

(22) PCT Filed: Mar. 14, 2013

(86) PCT No.: PCT/US2013/031712
§ 371 (c)(1),
(2) Date: Jun. 5, 2014

(87) PCT Pub. No.: WO2014/142926
PCT Pub. Date: Sep. 18, 2014

(65) Prior Publication Data
US 2015/0102214 A1    Apr. 16, 2015

(51) Int. Cl.
| | |
|---|---|
| *A61B 18/08* | (2006.01) |
| *A61B 18/04* | (2006.01) |
| *G01N 27/62* | (2006.01) |
| *G01N 21/64* | (2006.01) |
| *G01N 33/48* | (2006.01) |
| *H01J 49/00* | (2006.01) |
| *A61B 18/14* | (2006.01) |
| *A61B 18/00* | (2006.01) |
| *A61B 19/00* | (2006.01) |
| *A61B 17/32* | (2006.01) |

(52) U.S. Cl.
CPC .............. *G01N 27/62* (2013.01); *A61B 18/082* (2013.01); *A61B 18/14* (2013.01); *G01N 21/6486* (2013.01); *G01N 33/48* (2013.01); *H01J 49/0031* (2013.01); *A61B 17/320068* (2013.01); *A61B 18/042* (2013.01); *A61B 2018/00547* (2013.01); *A61B 2018/00595* (2013.01); *A61B 2018/00898* (2013.01); *A61B 2018/00904* (2013.01); *A61B 2018/146* (2013.01); *A61B 2018/1412* (2013.01); *A61B 2019/462* (2013.01); *A61B 2019/542* (2013.01); *A61B 2218/006* (2013.01)

(58) Field of Classification Search
CPC .............. A61B 18/082; A61B 18/042; A61B 2018/00898; A61B 2018/00904; G01N 33/4833
See application file for complete search history.

(56) References Cited

U.S. PATENT DOCUMENTS

| | | | |
|---|---|---|---|
| 5,192,267 A * | 3/1993 | Shapira et al. | 604/22 |
| 5,417,655 A | 5/1995 | Divilio et al. | |
| 5,550,214 A * | 8/1996 | Eberlein et al. | 530/328 |
| 5,701,899 A | 12/1997 | Porter | |
| 5,897,321 A * | 4/1999 | Goodman et al. | 433/215 |
| 6,146,353 A | 11/2000 | Platt, Jr. | |
| 6,221,337 B1 | 4/2001 | Dugstad et al. | |
| 6,377,841 B1 | 4/2002 | Lin et al. | |
| 6,506,550 B1 * | 1/2003 | Fulton et al. | 435/4 |
| 7,879,034 B2 * | 2/2011 | Woloszko et al. | 606/48 |
| 8,027,814 B2 | 9/2011 | Beyette et al. | |
| 2002/0106643 A1 | 8/2002 | Kulseth et al. | |
| 2003/0157025 A1 | 8/2003 | Unger et al. | |
| 2006/0069387 A1 * | 3/2006 | Gedebou | 606/45 |
| 2006/0292559 A1 * | 12/2006 | Reddy et al. | 435/5 |
| 2007/0179343 A1 * | 8/2007 | Shelokov | 600/205 |
| 2008/0319441 A1 * | 12/2008 | Seid | 606/42 |
| 2009/0030323 A1 | 1/2009 | Fawzi et al. | |
| 2010/0036373 A1 * | 2/2010 | Ward | 606/34 |
| 2010/0076411 A1 * | 3/2010 | Wu | 604/540 |
| 2010/0094282 A1 * | 4/2010 | Kabaya et al. | 606/42 |
| 2010/0144641 A1 * | 6/2010 | Popel et al. | 514/13 |
| 2010/0185139 A1 * | 7/2010 | Stearns et al. | 604/26 |
| 2010/0191083 A1 * | 7/2010 | Parker et al. | 600/347 |
| 2011/0020429 A1 * | 1/2011 | Lauten et al. | 424/450 |
| 2011/0077645 A1 * | 3/2011 | Lin | 606/45 |
| 2011/0087218 A1 * | 4/2011 | Boudreaux et al. | 606/41 |
| 2011/0295250 A1 * | 12/2011 | Johnson et al. | 606/41 |
| 2012/0156712 A1 | 6/2012 | Takats | |
| 2012/0244078 A1 | 9/2012 | Rychak | |
| 2012/0295286 A1 | 11/2012 | Berg | |
| 2012/0303016 A1 | 11/2012 | Fischer et al. | |

FOREIGN PATENT DOCUMENTS

| | | | |
|---|---|---|---|
| WO | WO-00/42988 | 7/2000 | |
| WO | WO-2010/136887 | 12/2010 | |
| WO | WO 2010136887 A1 * | 12/2010 | G01N 1/02 |

(Continued)

OTHER PUBLICATIONS

"Surgical Smoke," Clinical Notes, accessed at http://web.archive.org/web/20120106012236/http://www.surgin.com/PDF%20articles/whitepaper_surgin_clearflow.pdf, Surgin Inc., pp. 1-4 (2012).

Arii, S., et al., "Surgical strategies for hepatocellular carcinoma with special reference to anatomical hepatic resection and intraoperative contrast-enhanced ultrasonography," Oncology, vol. 78, Suppl 1, pp. 125-130 (2010).

Balog, J., et al., "Identification of Biological Tissues by Rapid Evaporative Ionization Mass Spectrometry," Analytical Chemistry, vol. 82, No. 17, pp. 7343-7350 (2010).

(Continued)

*Primary Examiner* — Phillip A Johnston
*Assistant Examiner* — Sean Luck
(74) *Attorney, Agent, or Firm* — Foley & Lardner LLP

(57) ABSTRACT

A method includes assessing tumor margins and discriminating between tumor and non-tumor tissues by analyzing the compositional make-up of smoke produced during cautery resection of tissues.

15 Claims, No Drawings

(56) References Cited

FOREIGN PATENT DOCUMENTS

| WO | WO 2011095253 A1 * | 8/2011 |
|----|---------------------|--------|
| WO | WO-2012/143739 | 10/2012 |

OTHER PUBLICATIONS

Donadon, M., and Moriss-Stiff, G., "New Paradigm in the Management of Liver-Only Metastases From Colorectal Cancer," Gastrointest Cancer Res, vol. 1, No. 1, pp. 20-27 (2007).

Gazelle, G.S., et al., "Tumor Ablation with Radio-frequency Energy," Radiology, vol. 217, pp. 633-646 (2000).

Hagan, P., "Scalpel that sniffs out cancer and removes tumour cells could boost patient survival rates," accessed at http://www.dailymail.co.uk/health/article-1221570/Scalpel-sniffs-cancer-The-new-surgical-tool-ensures-tumour-cells-removed.html, Oct. 20, 2009, 2 pages.

Hakim, M., et al., "Volatile Organic Compounds of Lung Cancer and Possible Biochemical Pathways," Chemical Reviews, vol. 112, No. 11, pp. 5949-5966, American Chemical Society (2012).

Hinz, K.P., et al., "Characterization of surgical aerosols by the compact single-particle mass spectrometer LAMPAS 3," Anal Bioanal Chem, vol. 401, No. 10, pp. 3165-3172 (2011).

Hinz., K-P., et al., "Analysis of surgical aerosols by on-line single particle and high resolution mass spectrosmetry," p. 1, (Feb. 15, 2012).

Iancu, C., et al., "Enhanced laser thermal ablation for the in vitro treatment of liver cancer by specific delivery of multiwalled carbon nanotubes functionalized with human serum albumin," Int J Nanomedicine, vol. 6, pp. 129-141 (2011).

International Search Report and Written Opinion for International Application No. PCT/US2013/031709 mailed on May 23, 2013.

International Search Report and Written Opinion for International Application No. PCT/US2013/031712 mailed on May 23, 2013.

International Search Report and Written Opinion for International Application No. PCT/US2013/031717 mailed on May 23, 2013.

Kishi, Y., et al., "Hepatocellular carcinoma: current management and future development-improved outcomes with surgical resection," International Journal of Hepatology, Article ID 728103, pp. 1-10 (2011).

Koch, M., et al., "Detection of Hematogenous Tumor cell Dissemination Predicts Tumor Relapse in Patients Undergoing Surgical Resection of Colorectal Liver Metastases," Annals of Surgery, vol. 241, No. 2, pp. 199-205 (2005).

Kouremenos, K.A., et al., "Advances in Gas Chromatographic Methods for the Identification of Biomarkers in Cancer," Journal of Cancer, vol. 3, pp. 404-420 (2012).

Mashir, et al., "Medical Applications of Exhaled Breath Analysis and Testing," PCCSU, accessed at http://www.chestnet.org/Education/Products/e-Learning/Medical-Applications-of-Exhaled-Breath-Analysis-and-Testing, vol. 25, Lesson 3, 8 pages.

Nguyen, K.T., et al., "World review of laparoscopic liver resection-2,804 patients," Ann Surg, vol. 250, No. 5, pp. 831-841 (2009).

Nguyen, Q.T., et al., "Surgery with molecular fluorescence imaging using activatable cell-penetrating peptides decreases residual cancer and improves survival," Proceedings of the National Academy of Sciences of the United States of America, vol. 107, No. 9, pp. 4317-4322 (2010).

Rees, M., et al., "One hundred and fifty hepatic resections: evolution of technique towards bloodless surgery," Br J Surg, No. 83, No. 11, pp. 1526-1529 (1996).

Rey, J.M., et al., "Spectroscopic investigation of volatile compounds produced during thermal and radiofrequency bipolar cautery on porcine liver," Measurement Science and Technology, vol. 19, No. 7, pp. 229-232 (2008).

Yao, P., and Morris, D.L., "Radiofrequency ablation-assisted liver resection: review of the literature and our experience," Hepato Pancreato Biliary, vol. 8, No. 4, pp. 248-254 (2006).

* cited by examiner

IDENTIFICATION OF SURGICAL SMOKE

CROSS-REFERENCE TO RELATED APPLICATIONS

This application claims the benefit under 35 U.S.C. §371 of International Application Ser. No. PCT/US2013/031712, filed on Mar. 14, 2013, the entire disclosure of which is hereby incorporated by reference for all purposes in its entirety as if fully set forth herein.

FIELD

The present technology relates generally to the analysis of cautery smoke from surgical and post-surgical procedures. The present technology further relates to the use of a marker for assessing the completeness of tumor resection in a subject.

BACKGROUND

The accurate diagnosis of a cancer condition relics on histological or cytological examination of tissue or cells respectively. Both laboratory techniques are time consuming, costly and do not provide the surgeon, in real-time, information necessary to discriminate between tumor tissue and non-tumor tissue. Histopathology and cytopathology are also ineffective at providing, in real-time, information necessary for assessing tumor margins or real-time information that permits differentiation between cancerous tissue and non-cancerous tissue during or post-surgery.

Additionally, the completeness of tumor removal depends in large part on the surgeon's ability to differentiate tumor tissue from normal tissue using subjective criteria. Modern surgical techniques used in tumor removal use a variety of surgical instruments. Some of those instruments generate smoke and fumes that may be used to differentiate between tumor tissue and normal tissue. However, the generation of smoke and fumes can cause problems for the surgical staff participating in the surgery. For instance, surgical smoke is known to impair the visual field of the surgeon, produce undesirable odor, and even cause the release and dissemination of noxious chemicals or particles that can have harmful health effects on healthcare workers. Thus, the capture of the smoke and fumes from surgical equipment may not only be beneficial to the operating room workers, but also provide valuable information regarding the completeness of the surgical procedure.

SUMMARY

In one aspect, a method is provided for assessing tumor margins during surgery in a subject undergoing resection by cauterizing along visual boundaries of a tumor to generate gaseous tissue particles; analyzing the gaseous tissue particles to determine a compositional make-up of the gaseous tissue particles; and comparing the compositional make-up of the gaseous tissue particles to a predetermined value of the compositional make-up of one or more non-tumor tissues. In such methods, the surgeon will discontinue cauterization when the compositional make-up of the gaseous tissue particles corresponds to the compositional make-up of one or more non-tumor tissues. The method may use a thermal cautery or a radiofrequency bipolar cautery to resect tumor tissue. The resection may be carried out during surgery or in an out-patient facility.

In another aspect, a method is provided for assessing tumor resection post surgery. Accordingly, after the surgeon has removed what is believed to be a tumor, the tissue mass that is removed may be scanned on its surface by a cautery or other smoke or particle generator, and the smoke and/or particles are tested for a compositional make-up. The absence of smoke or gaseous tissue particles that correspond to tumor markers indicates a successful surgical procedure in that the tumor margins were not breach and wholly contained with the tissue mass that was removed. Conversely, the present of smoke or gaseous tissue particles that correspond to tumor markers indicates that the tumor margin may have been breach during resection and that further surgical intervention may be warranted.

According to the above aspects, the methods include differentiating tumor tissue from non-tumor tissue by capturing a smoke and/or vapor emitted during cauterization of tissue; analyzing the smoke or vapor to detect the presence of at least one chemical marker or bio-marker associated with tumor tissue; and differentiating between tumor tissue and non-tumor tissue based on the presence or absence of the marker in the captured smoke.

In certain embodiments, the marker associated with tumor tissue is a chemical marker selected from the group consisting of $C_1$-$C_{20}$ alkanes, aldehydes, ketones, ammonia, and $C_1$-$C_4$ alcohols. For instance, the presence of ethane in cautery smoke may be indicative of breast cancer tissue when resecting from the breast region of a subject, or the presence of methane or ethane in the cautery smoke may be indicative of liver cancer tissue when resecting the liver of the subject. On the other hand, the presence of aldehydes in the cautery smoke may be indicative of prostate cancer when resecting the prostate of a male subject.

In any of the above embodiments, the marker associated with tumor tissue may be a biomarker. Exemplary of such markers include carbon monoxide, dinitrogen oxide, nitric oxide, hydrogen, glucose, dihydroxyacetone phosphate, glyceraldehyde-3-phosphate, lactate, pyruvate or nicotinamide adenine dinucleotide (NADH). According to an embodiment of the method, the presence of NADH in surgical smoke is indicative of a malignant tumor tissue.

In another aspect, a method is provided for assessing the progression of a cancer condition by analyzing a cautery smoke to detect the presence and/or concentration of at least one chemical marker, or bio-marker, known to be associated with a cancer condition; and using such information to assess the progression of a cancer condition. The method may also include comparing the concentration of at least one chemical marker or bio-marker present in cautery smoke.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. Tf there are uses of the term which are not clear to persons of ordinary skill in the art, given the context in which it is used, "about" will mean up to plus or minus 10% of the particular term.

"Alkyl" or "alkane" refers to straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

When tissue is cauterized, superheating leads to the formation of a plasma. As the superheating and plasma of the tissue is established, charring, vaporization and/or ionization of the tissue occurs thereby generating a combination of smoke, particles, and vapors that may rise from the site of cauterization. Typically, the site of cauterization is associated with a surgical site. Any one or more of the smoke, particles, or vapors are referred to herein generally as "cautery smoke." The cautery smoke may contain mixtures of chemical and biochemical components, gaseous tissue particles and other particulate matter such as cells, cellular debris and viruses. The present technology provides for the analysis of the cautery smoke and the gaseous tissue smoke, particles, and vapors associated therewith, as they are generated by a variety of cautery, or other surgical, devices. Such surgical devices routinely used to remove diseased or cancerous tissue from the body include, but are not limited to, cautery devices, harmonic scalpels, plasma blades, monopolar electrocautery scissors, and bipolar electrothermal cauterizers and sealers. Such diseased or cancerous tissue may arise from a disease state that may include, but is not limited to cancer states of a wide variety. For example, the disease states may be present as cancerous tissue or tumor tissue. The cancerous tissue or benign tumor tissue may include, but is not limited to breast cancer, liver cancer, bone cancer, lung cancer, brain cancer, intestinal cancer, testicular cancer, ovarian cancer, colon cancer, and other cancers as are known.

As used herein, the terms cautery, cauterization, cauterized, cautery smoke, or cautery vapor may also refer to processes conducted with non-thermal cutting devices which may only produce a mist or a vapor as a result of tissue destruction. For example, ultrasound scalpels operate by vibrating one blade against a stationary blade at a high frequency. Cutting is achieved by mechanical denaturation of proteins, and the temperatures only rise to approximately 80° C. Accordingly, there is no boiling of water, however a fine mist is released at the cutting site while the denatured tissue and collagen mixes with water to form a glue that effectively adheres the tissue together and closes the cut. Thus, while ultrasonic or ultrasound scalpels do not superheat the tissue, they are defined herein as cautery devices due to their vapor/mist generation effects. The vapor/mist generated by an ultrasonic or ultrasound scalpel is expressly defined herein to be encompassed by the term "cautery smoke" as that term is defined herein and may more generally be used. In some embodiments, the surgical device is a Bovie knife or ultrasound scalpel.

The analysis of the cautery smoke may be conducted during surgery to remove tissue, or after the surgery to determine the success of the surgery. For example, during a surgical procedure to remove tissue, a cautery may be used that cuts and cauterizes tissue resulting in tissue resection and blood loss minimization. The cautery smoke that is generated may be removed from the surgical site and analyzed to determine the compositional makeup of the tissue that has been cut. In such a procedure, the surgeon, or other medical professional, resects the cancerous or tumor tissue. If during resection, the analysis of the cautery smoke indicates that cancerous or tumor tissue has been breached, the surgeon may be advised and can re-direct the resection to avoid the cancerous or tumor tissue to result in complete removal. In such a procedure, the goal is to remove the cancerous or tumor tissue without contacting the cancerous or tumor tissue. The advisement of the surgeon may be through visual indicators, for examples graphs or numbers displayed on a screen indicating a substantive change in the compositional makeup of the cautery smoke. The advisement of the surgeon may be through auditory indicators with sounds generated to indicate a substantive change in the compositional makeup of the cautery smoke. The advisement of the surgeon may be through physical indicators with a vibration of the surgical cautery device to indicate a substantive change in the compositional makeup of the cautery smoke.

Alternatively, or in addition to the above, the analysis of the cautery smoke may be conducted after the surgery to determine the success of the surgery. For example, during a surgical procedure to remove tissue, the surgeon may use a non-cautery device, such as scalpel or other cutting instrument, to remove diseased and/or cancerous or tumor tissue from a subject. The removal is effected by the surgeon cutting through tissue adjacent to, but not within, the diseased and/or cancerous or tumor tissue, such that a tissue mass is removed. A cautery may be then be used to sample the outer surface of the tissue mass to determine if the tissue at the outer surface is normal tissue (i.e. non-diseased and/or non-cancerous or non-tumor tissue) or if it is diseased and/or cancerous or tumor tissue. Such sampling may be conducted by the surgeon or other medical professional that is trained in such sampling procedures. In such a process, the cautery device is used to generate a cautery smoke (including smoke, particles, and vapors) and the cautery smoke is analyzed for substantive changes in the composition makeup of the tissue when compared to a normal baseline value for normal tissue. If the tissue is normal, then the surgeon has standing to believe that the known diseased and/or cancerous or tumor tissue was successfully removed. However, if the surface of the tissue mass is found to contain diseased and/or cancerous or tumor tissue, the surgeon may have reason to believe that the non-normal tissue was breached and that further surgical intervention may be warranted.

As noted, a baseline level of a chemical or biological marker in a patient may be initially determined. Accordingly, at the beginning of a surgical procedure, or in pre-operative planning stages, known "normal" (i.e. non-cancerous, non-tumor) tissue near the tumor site, but which is clearly free of tumor tissue, may be sampled with the cautery or other surgical device. The cautery smoke, particles, and vapors that are generated are then sampled to determine a baseline concentration of the various chemical and biological markers that are detected. This baseline may then be used to set the baseline level for which surgical or post-surgical cautery testing is then compared to in determining whether or not certain disease states, or if cancerous or tumor tissue, are present.

Alternatively, the baseline level of the components of cautery smoke that are to be monitored, may be a standard baseline level that is determined from a wide range of samplings from a wide range of subjects, with the baseline level being an average or a range. In other words, large sampling databases may be obtained to determine baseline levels on average for a large group of subjects. The large sampling databases may then be the basis for comparison of the various chemical and biological markers in the tissue to which individual subject are compared during, or after surgical procedures to remove tumor or cancerous tissue.

The analysis of cautery smoke may be performed using any chemical or biochemical method including mass spectrometry, cavity ring-down spectrophotometeric gas analysis, Raman spectroscopy, photoacoustic technologies, gas chromatography, or rapid evaporative ionization mass spectroscopy (REIMS). In the methods, a sample of cautery smoke is introduced into a mass spectrometer, gas chromatography analyzer, or photoacoustic analyzer to determine the compositional make-up of the cautery smoke. The gas chromatography analyzer or spectrophotometer may be employed to provide real-time analysis of the compositional make up of cautery smoke. The gas chromatograph may also employ an electron capture detector, a sampling ion trap detector, or a negative ion capture detector, to detect and analyze trace gases in the smoke or vapor.

To permit real-time analysis of cautery smoke, a cautery device, or other thermal surgical device, may be fitted with a smoke extraction device near the cutting tip of the device. The smoke extraction device contains a hollow tubular body having a lumen, that is adapted to be connected at one end to a vacuum source, and contains an attachment member for receiving the cautery device at the end of the tubular body opposite to the end connected to the vacuum source. The smoke produced during cauterization of tissue can be periodically, or continuously, evacuated from the surgical site by the application of the vacuum. The smoke is then evacuated through the lumen of the hollow tubular body and conveyed to the spectrophotometer or gas chromatograph, where the compositional make-up of the smoke is analyzed.

The present technology permits, therefore, real-time assessment of tumor margins by comparing the compositional make-up of the gaseous tissue particles to a predetermined value of the compositional make-up of gaseous tissue particles from one or more non-tumor tissues.

As introduced above, cautery smoke has a compositional makeup that includes smoke, particles, and vapors. Included in those materials may be one or more chemical markers, one or more biological markers, or a combination of such substances as identifiers specific to one or more disease states. Such markers may be endogenous to the individual, meaning that the markers are produced by the subject and are associated with the normal and/or diseased tissue. Such markers may also be exogenous to the individual, meaning that the markers are purposefully added to the subject as a marker or tracer that becomes associated with the diseased tissue.

For instance, chemical may include, but are not limited to, $C_1$-$C_{20}$ alkanes or aldehydes, the presence of which in tissue and accordingly in the cautery smoke may be indicative of cancer. The presence of a $C_1$-$C_{20}$ alkane, in an amount that is greater than a pre-determined baseline value in cautery smoke, may indicate that the cautery, or other surgical device has contacted cancerous tissue. In one embodiment, when resecting potentially diseased tissue from a breast, the presence of $C_1$-$C_{20}$ alkanes may be indicative of breast cancer. In another embodiment, when resecting tissue associated with a prostate, the presence of $C_1$-$C_{20}$ aldehydes in cautery smoke may be indicative of cancerous prostate tissue.

In addition to alkanes and aldehydes, cautery smoke may contain other chemical agents, for example, ketones, alcohol and ammonia whose presence above a predetermined levels in cautery smoke are indicative of other disease states. Thus, the presence of alcohol in cautery smoke, above a predetermined baseline level, may be indicative of liver disease.

In addition to the chemical markers described above (i.e. the alkanes, aldehydes, alcohols, ketones, and ammonia), cautery smoke can contain a variety of other endogenous biological substances, or markers, whose presence is considered to be indicative of certain disease states. Illustrative biological markers may include, but are not limited to, carbon monoxide, dinitrogen oxide, nitric oxide, hydrogen, glucose, dihydroxyacetone phosphate, glyceraldehyde-3-phosphate, lactate, pyruvate or nicotinamide adenine dinucleotide. (NADH). While each of these may also be present in cautery smoke from normal tissue, an enhanced amount above a baseline level is considered to be indicative of a disease state, for example, a cancerous condition. Thus, the presence of a cancerous tissue can determined by characterizing and quantifying the one or more of endogenous biological markers within the cautery smoke. As an example, the presence of NADH in cautery smoke is considered to be indicative of a malignant cancer condition.

Pairings of chemical markers, biological markers or a chemical marker and a biological marker may also be used for differentiating between tumor and non-tumor tissue or to indicate progression of a cancer condition. For example, the presence of both an aldehyde and NADH in cautery smoke may signal malignancy of prostate tumor, particularly, if the concentration of these two markers is greater than a predetermined baseline level that is correlated to progression of a prostate cancer condition.

Exogenous substances may also be introduced to a subject either generally, or directly to diseased tissue. For instance, a subject undergoing surgical intervention can be administered a tumor-specific marker (e.g. a compound that is specific for a particular type of tumor tissue) prior to surgery. During resection, contact of the tissue with a cautery pen or knife causes superheating of tissue that results in vaporization of the tissue. Because the marker concentrates to a greater extent in tumor tissue than surrounding normal tissue, the level of marker in cautery smoke will depend on whether the cautery pen or knife contacts tumor tissue or non-tumor tissue. It follows therefore, that the presence of the marker in cautery smoke or cautery vapor or a pyrolysis product of the tumor marker, in the cautery smoke indicates contact of the cautery with tumor tissue while the absence of the marker in cautery smoke or vapor indicates contact of the cautery with non-tumor tissue.

It will also be appreciated that general administration of such a marker to a subject, will not result in defined lines of concentrations of the marker in the cancerous versus non-cancerous tissue. There will likely be a gradient in the amount of marker with higher concentrations at the diseased or cancerous tissue with lower, radiating amounts from such tissue. Accordingly, it may be that the cautery develops a gradient increase which may then be calibrated to a known gradient of the particular marker in tissue to determine how close to the diseased tissue the surgeon has resected.

The marker may or may not be compound that is exogenous or endogenous to the subject. For example, during cauterization, and due to the heat that is associated with such processes, the tissues and any markers or compounds therein are subject to heating. As those tissue and any markers or compounds therein begin to vaporize and char, they are released from the surface of the tissue not only as the marker or compound therein, but as degraded products as well. For example, while the marker may be one material in the subject, under heating it will produce a signature of other oxidized or other degraded compounds that is then detected by the analysis instrument.

Tumor-specific markers may also be used to mark or trace tumor tissue. Illustrative tumor-specific markers include, but are not limited to, radiolabeled compounds that bind a specific protein expressed on tumor cells, fluorescent or radiolabeled tumor selective peptides, fluorescently labeled compounds, radiolabeled compounds, fluorescent dyes, fluorescent or radiolabeled cell penetrating peptides specific for an intracellular tumor protein, fluorescent or radiolabeled tumor-specific antibodies, fluorescent or radiolabeled proteins, or any chemical/biochemical agent that can bind tumor tissue or non-tumor tissue so as to permit the surgeon a detectable identifier for discriminating between tumor and non-tumor tissue.

The tumor-specific marker can also be a compound, peptide, dye or an antibody that is conjugated to a nanoparticle, a magnetic particle or a particle made using a biopolymer. In certain embodiments, the tumor-specific marker is contained within a particle made of a biopolymer that decomposes upon reaching a tumor tissue to release the tumor-specific marker at the site of tumor tissue.

Active labeling and passive labeling of tumors can be achieved using any one of the above mentioned agents. Labeling of tumor will depend on the kinetics of transport of the labeling agent to the tumor site and the transport of the labeling agent into tumors across the cellular membrane which can take place passively or actively. Passive transport relies on the ability of the labeling agent to diffuse across the lipid bilayer, while active transport requires the labeling agent to first bind to a cell surface receptor and the energy dependent transport of the receptor-label complex across the cell membrane into cells. Whether passively or actively transported, once inside the cell, the labeling agent will bind to an intracellular organelle or protein, preferably, a protein that is over-expressed in tumor cells versus normal cells so as to selectively concentrate and label tumor cells.

As introduced above, the marker(s) may be administered prior to surgery, allowing sufficient time for the marker to become associated with the tumor tissue. Administration of a pharmaceutical composition containing the tumor-specific marker can be through an intravenous route, orally, through an intratumoral injection, or intraperitoneally. The marker is then permitted to bind to, or become associated with, tumor tissue prior to surgery. Thus, in one embodiment of the present method administration of the tumor marker is followed by a wait period to permit the transport and binding of the marker to tumor tissue. The time interval between administration of the tumor marker and surgery may vary from seconds to about a few minutes to a few hours depending on the kinetics of transport of the marker to tumor tissue. In some embodiments, the time interval is from about 1 min to about 180 minutes. In some embodiments, the time interval is about 5 minutes. In some embodiments, the time interval is about 10 minutes. In some embodiments, the time interval is about 15 minutes. In some embodiments, the time interval is about 20 minutes. In some embodiments, the time interval is about 30 minutes. In some embodiments, the time interval is about 45 minutes. In some embodiments, the time interval is about 60 minutes. In some embodiments, the time interval is about 75 minutes. In some embodiments, the time interval is about 90 minutes. In some embodiments, the time interval is about 120 minutes. In some embodiments, the time interval is about 150 minutes. In some embodiments, the time interval is about 180 minutes.

Thus, to assess completeness of tumor resection using an exogenously administered tumor-specific marker, a subject suffering from a cancer condition is administered such a marker, namely, a compound, dye, peptide, antibody or any combination of these reagents that bind tumor tissue to a greater extent than normal tissue. After waiting for a specific interval of time to promote association between the marker and tumor tissue as well as marker and non-tumor tissue, the subject will undergo surgery. As described above, the cauterization may be conducted along the visual boundaries of a tumor will result in the production of cautery smoke, a gaseous mixture that includes tissue particles (gaseous tissue particles), cellular materials, cell debris and one or more compounds used as the marker. This mixture of gaseous tissue particles can be analyzed to quantify the concentration of marker at the site of cauterization. Alternatively, the surgeon may remove the tumor tissue without non-cautery cutting devices, and then analyze the outer surface of the resected tissue with the cautery to determine of the tumor was, or was not, breached by the non-cautery cutting device. By comparing the concentration of marker in gaseous tissue particles to predetermined values for concentration of the same marker in cautery smoke obtained from non-tumor tissues a surgeon can evaluate the completeness of tumor resection. Because the affinity of the marker is greater for tumor tissue, the concentration of marker in the gaseous tissue particles should be higher when the cautery is contacted with tumor tissue. It follows therefore, that tumor resection is deemed to be complete when the concentration of a marker in gaseous tissue particles equals or is less than the concentration for the same marker in cautery smoke from a normal tissue.

While agents used as tumor markers can directly be formulated in a physiologically acceptable diluent for administration to a patient by one of the aforementioned delivery routes, microbubbles containing one or more signaling agents as detectable tags for tumor tissue can also be used as delivery vehicles. According to one method for identifying tumor tissue during surgical resection, a patient suffering from a diseased state is administered prior to surgery, a pharmaceutically acceptable composition of microbubbles that contain one or more tumor-signaling agents. Following administration of the tumor-binding agents, the patient undergoes surgical resection of the tumor either with, or without a cautery as described above. As the surgeon, or cautery operator, cauterizes along the visual boundaries of the tumor, heat from the cautery vaporizes the tissue and disrupts the microbubbles that may be bound to the tissue, thereby generating or releasing a gaseous mixture of tissue particles and vapors of the tumor signaling agent in the resulting cautery smoke. This gaseous mixture can be analyzed to determine the presence and concentration of tumor signaling agent, a detectable signature of the tumor-signaling agent, a detectable by-product of the tumor signaling agent or any combination of these to identify the tissue being cauterized as tumor tissue or non-tumor tissue. Alternatively, the surgeon may resect the tumor with a non-cautery device and then later analyze the resected tissue for the presence, or absence, or gradient concentration of the signaling agent.

The microbubbles containing one or more tumor signaling agents may be spheres composed of a lipid bilayer that encapsulates one or more signaling agents. The microbubbles may be contacted with a tumor tissue passively or via active tagging of the cancerous tissue. In one embodiment, the lipid surface of the microbubbles may be attached to one or more biological substances, such as an antibody that is specific for tumor cells so as to facilitate active binding and increased concentration of the microbubbles to corresponding antigens on cancer cells. The microbubbles may have a vascular half-life of a few minutes to a few hours and can be formulated as pharmaceutically acceptable compositions for intravenous administration to a patient. The vascular half-life of the microbubbles, therefore, may be from about 5 minutes to about 24 hours, for instance, about 15 minutes, about 30 minutes, about 60 minutes, or about 90 minutes. In certain embodiments the vascular half-life of the microbubbles may be from about 2 hours to about 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, or 3 hours.

Sampling of the cautery smoke can be performed periodically or continuously for the presence of tumor signaling agent. By measuring the concentration of the tumor signaling agent in cautery smoke and comparing the measured concentration to pre-determined values for concentration of the same signaling agent from non-cancerous tissue, a visual score can be computed that would permit intra-operative determinations of anatomical margins thereby enabling superior management of tumor resection procedures. Because cancer cells divide more rapidly than normal cells, cancerous tissue is more vascularized than normal tissue. The greater vasculature of cancer tissue permits higher concentrations of the microbubbles containing the tumor signaling agent to bind cancerous tissue, thus, enhancing sensitivity of tumor detection.

As described above, any agent that selectively binds to cancer cells or is more selectively transported into cancer cells can be used as the tumor signaling agent. The signaling agent can be in the form of a solid, liquid or gas and can contain more than one detectable groups. Illustrative signaling agents may include, but are not limited to perfluorinated alkanes, such as, but not limited to, perfluoroethane, perfluoropropane, perfluoro-isopropane, perfluorobutane, perfluoro-isobutane, perfluoro-tertiarybutane, perfluoropentane, perfluoro-isopentane, perfluorohexane, perfluorooctyl bromide, or perfluoro-neopentane; or gases such as, but not limited to, sulfur hexafluoride.

The signaling agent may be a compound that can be detected directly without thermal transformation or is produced by the thermal breakdown of a molecule within the microbubble during cauterization. Thus, contacting the tumor tissue with a cautery pen or knife can cause the tissue to heat up, ionize and/or vaporize causing the microbubbles attached to or within the vicinity of the tumor tissue to disrupt as a result of the radiated heat. Disruption or bursting of the microbubbles releases and vaporizes the signaling agent causing it to be a part of cautery smoke or vapor. To promote thermal disruption of the microbubbles during cauterization, thermally degradable polymers will be used for the manufacture of the microbubbles. While any source capable of providing thermal energy can be used to ablate the microbubbles, in one embodiment, the use of cautery for disrupting the microbubbles and releasing the tumor-specific signaling agent is provided. Illustrative of the class "thermally degradable polymers" are polymers or copolymers of optionally substituted cyanoacrylates, such as methylcyanoacrylate, methoxyethyl cyanoacrylate, polymethacrylic acid and polyethylene glycol.

To identify whether the tissue being cauterized is cancerous or non-cancerous, a subject is administered a composition or microbubbles containing perfluorobutane that bind to, or associate with, tumor cells, for example, in the liver. Because the microbubbles containing perfluorobutane preferentially migrate, and potential bind, to tumor cells, resection and cauterization of the hepatic tissue will promote release of the perfluorobutane which can be detected by instrumentation associated with the cautery knife Both periodic or continuous analysis of the cautery smoke for the presence and concentration of the signaling agent can be carried out by the surgeon or cautery operator. Because perfluorobutane is not a naturally occurring substance in the body, it and its thermal degradation products may only be attributable to the composition of microbubbles administered to the patient prior to surgery.

In one embodiment, the captured smoke or vapor is analyzed through the use of in situ or laboratory optical spectrophotometry, mass spectroscopy, gas chromatography, Raman spectroscopy or other known techniques. When the perfluorobutane, or degraded or oxidized product thereof is detected, the analytical instrument triggers an audio, visual, or physical response to inform the surgeon, or cautery operator in real time of the presence of the perfluorobutane marker, thereby indicating the presence of hepatocellular carcinoma cells. Likewise, if the instrument does not detect perfluorobutane, or degraded or oxidized product in the cautery smoke, it may use a different audio or visual cue to inform the surgeon to change course along which resection is being performed so as to determine if all of the tumor tissue is removed, or if additional cauterization is required.

In addition to using microbubbles to tag tumor tissue, the present technology also provides a method for differentiating between tumor and non-tumor tissue by administering to a patient perfluorobutane or fluorescent dye containing microbubbles that are surface functionalized to preferentially bind and internalize in normal cells. According to this aspect of the technology, the instrument analyzing cautery smoke will provide an audio or visual cue when the cautery is in contact with non-tumor tissue while the absence of an audio-visual signal will implicate contact of the cautery with tumor tissue.

Changes in any of the above marker levels or signaling agent levels during, or after, surgical resection of tumor, such as an increase or decrease in the concentration of the marker in cautery smoke also can be monitored and a surgeon can be alerted to such changes in marker levels using audio, visual, and physical cues such as a video panel, indicator lights, alert sounds, vibrations, or other means of communication. In one exemplary embodiment spectroscopic analysis of the cautery smoke permits the quantification of the marker in real-time as the surgeon moves the cauterization blade through tissue and converts the measured concentration to a cancer score between 0% and 100%. By selecting a threshold value of this score, for example, in the range from about 90%-100%, 90%-98%, 90%-96%, 90%-94%, or 90%-92%, that is indicative of a cancerous condition, the surgeon may be alerted using visual, auditory, or physical cues whether the tissue being cauterized is cancerous or not, thus permitting real-time discrimination between tumor tissue and non-tumor tissue. Likewise, the absence of the tumor marker, or a pyrolysis product of the tumor marker, in the cautery smoke indicates contact of the cautery with non-tumor tissue. As stated above, any chemical, electrochemical, or biochemical method can be used to analyze the smoke produced upon contact of the cautery with tissue.

In one embodiment, therefore, a method for assessing completeness of tumor resection is provided. The absence of a biological marker, chemical marker, or signaling agent that is endogenous or exogenous to tumor tissue and is normally elevated in tumor tissue can be used as an indicator of complete tumor resection. According to this method, a surgeon resects along the tumor's visual boundary using a cautery pen or cautery knife. Such contact of tissue with the cautery pen or knife results in the generation of a gaseous mixture of tissue particles, chemical biomarkers and/or endogenous biological markers which can be captured and analyzed using any one of the analytical techniques further described below. The absence or a lower level of one or more endogenous biomarkers in cautery smoke indicates that the tissue contacted with the cautery pen or knife is not cancerous and is therefore indicative of complete tumor resection. In an alternative embodiment, a resected mass of tissue is analyzed with a cautery to determine if an outer surface of the tissue contains a biological marker, chemical marker, or signaling agent that is indicative of, or associated with, cancerous or diseased tissue. The absence of such a biological marker, chemical marker, or signaling agent may indicate that the resection was complete, while the presence of such a biological marker, chemical marker, or signaling agent may indicate that the resection was incomplete, or that the diseased tissue was breached.

In an alternative embodiment, a patient is administered a marker that is specific for normal tissue and therefore, will concentrate to a greater extent in normal tissue compared to tumor tissue. According to this aspect of the present technology, the cautery smoke is analyzed for the presence or absence of such a marker. Because the marker preferentially binds to normal tissue, the concentration of the marker in cautery smoke should be greater when tumor resection is complete, that is, the tissue being cauterized is normal tissue.

Methods for assessing the progression of a cancer condition are also provided. Information related to the concentration and identity of at least one chemical or biological marker known to be associated with a cancer condition can be used to assess the progression of a cancer condition. In one embodiment, information related to the concentration of tumor-specific markers is obtained by analyzing the cautery smoke for the presence of one or more known tumor-specific markers as the cautery device moves along the visual boundaries of the tumor during surgical resection. Accordingly, a higher concentration of one or more known tumor-specific markers in cautery smoke is indicative of a greater progression of the cancer condition. For example, high concentrations of nitric oxide or NADH in cautery smoke may signal progression of a cancer condition and malignancy in a subject. Such analysis may be performed within the operating room or the resected tumor can be transported to another room, such as a laboratory for analysis.

The present technology further provides a method for assessing tumor margins during surgery in a subject undergoing resection. Briefly, the method teaches cauterizing tissue along the visual boundaries of a tumor to generate cautery smoke having gaseous tissue particles. The gaseous tissue particles are then captured and analyzed to determine the compositional make-up of the cautery smoke. The smoke, vapor or other aerosols that are produced during cauterization may contain one or more chemical markers, one or more biological markers, or a combination of a chemical marker and a biological marker can be used as identifiers specific to tumor tissue. According to this method a surgeon will discontinue tissue cauterization when the compositional make-up of cautery smoke generated during surgical resection of tumor corresponds to a predetermined value of the compositional make-up of cautery smoke from normal tissue.

The present technology improves current cancer management practices that rely on surgical resection of cancerous tissue using cauterization and post-surgical chemical/biochemical analysis of the resected tissue to discriminate between tumor and non-tumor tissue. For example, surgical resection of a diseased liver or a diseased section of the liver is commonly conducted for treating hepatocellular cancers. Irrespective of whether the surgery is performed laparoscopically or liver resection is performed using an open surgical field, both procedures involve using a cautery knife to resect the diseased liver or a portion of the diseased liver. Such cauterization generates tissue particles, smoke and vapors, as well as other aerosols which can be analyzed in real-time for scoring a cancerous condition, identifying the onset of malignancy or discriminating between tumor tissue and non-tumor tissue.

The above described methods for identifying tumor tissue can readily be applied to liver resection surgeries presently considered to be the mainstay treatment protocol for hepatocellular carcinoma. The present diagnostic methodology also overcomes hurdles necessary for clinical approval by using microbubbles that are routinely used clinically for a variety of procedures including, but not limited to, contrast-enhanced imaging such as ultrasonography and magnetic resonance imaging (MRI). The methods provided herein take advantage of this body of work, and add further sensitive measurement techniques to enhance the ability of cauterization to remove all, or substantially all tumor tissue.

The use of microbubble encapsulated tumor signaling agents can also be used to determine the extent of tumor metastasis and thus permit the determination of the stage of a cancer condition. Accordingly, the surgeon will periodically or continuously monitor cautery smoke as the blade of a cautery knife or pen contacts tissue distal from the visual boundaries of the tumor as well as in other areas of the surgical field to quantify the concentration of tumor-specific signaling agent. In another embodiment, therefore, a method is provided for the intra-operative staging of a cancer condition by contacting a tumor tissue with microbubbles comprising a signaling molecule and cauterizing the tumor tissue to generate cautery smoke or cautery vapor. Staging of the cancer depends on the concentration of the signaling molecule in cautery smoke. According to this method a higher concentration of a signaling molecule in cautery smoke is indicative of a later stage of a cancer condition. For certain aspects of staging of a cancer condition, the method relies on using stabilized lipid microbubbles comprising a biological complement of a group expressed on the surface of the tumor tissue. Thus, for example, the biological complement may comprise an antibody while the tumor tissue comprises an antigen which is complementary to that antibody. The described method for staging is particularly suited to staging of cancerous hepatic tissue, cancerous renal tissue, cancerous pancreatic tissue, cancerous breast tissue, or cancerous prostate tissue.

Because the methods may be used to determine the stage of cancer, in one embodiment, the stage of a cancer condition is determined by comparing the concentration of signaling molecule in cautery smoke or cautery vapor to a pre-determined value of the signaling molecule from stage I to stage IV tumor tissues. For example, a higher concentration of the signaling molecule in cautery smoke or cautery vapor is indicative of a later stage of the cancer condition.

The present technology also provides a method for discriminating between tumor and non-tumor tissue whereby the microbubble containing one or more signaling agents is contacted with a tumor tissue during surgery, but prior to contact of a cautery pen or knife with the visual boundaries of a tumor.

The present technology, thus generally described, will be understood more readily by reference to the following examples, which are provided by way of illustration and are not intended to be limiting of the present invention.

EXAMPLES

Example 1

A patient diagnosed with hepatocellular carcinoma will be intravenously administered a solution of microbubbles that contain the detectable marker perfluorobutane and are functionalized to associate to a greater extent with tumor tissue than normal tissue. Following administration of the microbubble solution, the patient will undergo surgery to remove the cancer. The surgical cautery device used will be equipped with a smoke removal unit that is connected using a pump to a mass spectrometer unit that is modified to ionize and analyze the smoke generated during surgery.

Resection will be performed along the visual boundaries of the tumor tissue. Preferably the tumor will be resected together with parts of healthy skin and surrounding lymph nodes in order to minimize the chance for tumor recurrence. While resection will be performed along the visual boundaries of the tumor, these boundaries can be altered depending on the mass spectrometric analysis of cautery smoke produced as the tissue is being cut.

The mass spectrum of total ion current obtained during surgical intervention will be measured. The amount of marker in cautery smoke will be determined and if the measured amount exceeds a baseline value determined for healthy tissue the instrument analyzing the cautery smoke will generate an audio signal to inform the surgeon in real-time that the tissue being cauterized is tumor tissue. The baseline value will either be determined based upon known baseline values for a sampling of similar patients, or will be determined in adjacent healthy tissue to the disease tissue being resected. It should be noted that mass spectrometric signals are detectable only when actual surgical cutting is performed and not when the cautery or the surgical field is being cleaned.

Alternatively, the ratio of the concentration of marker in cautery smoke is compared to a predetermined concentration of marker in normal tissue and this quantity will be displayed on feedback device using audio, visual, or physical signals. For example, the surgeon may be made aware that the tissue in contact with the cautery is normal by a change in the frequency of a beeping sound when the cautery contacts non-tumor tissue. Post-surgical histological examination of removed material will prove that the present method improves efficiency of tumor removal.

Example 2

An electrosurgical unit will be used in combination with quadrupole ion trap mass spectrometer for analysis. Electrosurgical cutting electrode will be equipped with a smoke removal unit, which will be connected to fluid-pump using tubing. The fluid pump will be part of an instrumental set up that is equipped with secondary electrospray post-ionization unit, that includes a capillary, a high voltage power supply, electrospray, and a mass spectrometer operated in positive ion mode. Ions at m/z 447 and 449, or other m/z values, may be monitored with m/z 446 as background signal.

Nude mice carrying NCI-H460 human non-small cell lung cancer xenograft will be housed in a temperature- and light-controlled room, feed and water were supplied ad libitum. At age of 8 weeks, the mice will be dosed with 2×20 mg/bw kg gefitinib. Following 3 days of drug treatment, tumor xenografts will be sampled in vivo, under phenobarbital anesthesia. Electrosurgical cautery will be used to remove non-small cell lung cancer tumor and also to obtain healthy lung tissue. Both tumor bearing and non-tumor bearing mice will be subjected to preoperational chemotherapy using Gefitinib. Gefitinib (molecular weight is 446) selectively binds to epithelial growth factor receptor (EGFR), which is overexpressed by NSCLC tumor cells. Thus, gefitinib can be used for the chemical labeling of these tumors.

Tumors will be resected together with parts of healthy lung tissue. Tumor margins will be determined based on mass spectrometric identification of tissue being cut using a ratio for the concentration of ions at m/z 447 and m/z 446 in cautery smoke to the concentration for ions at m/z 447 and m/z 446 in normal tissue. These results will be displayed using a feedback device, which will translate the mass spectral data to a blue-red color gradient or an audio signal.

The above described methods can also be used to discriminate between tumor and non-tumor tissue using a fluorescently labeled antibody that binds a protein overexpressed by tumor cells. Cautery smoke containing the fluorescently labeled antibody or some derivative of it will be analyzed using a fluorimeter to quantify the fluorescent signal and compare it to a predetermined level of fluorescence from normal tissue.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

Other embodiments are set forth in the following claims.

What is claimed is:

1. A method for assessing the completeness of tumor resection in a subject, the method comprising:
    introducing to the subject a marker that binds tumor tissue to a greater extent than non-tumor tissue;
    cauterizing along the boundaries of a tumor to generate a cautery smoke; and
    comparing a concentration of the marker in the cautery smoke to a predetermined concentration for the marker in a non-tumor tissue to assess the completeness of tumor resections;
    wherein the tumor is completely resected before said cauterizing the tissue along the boundaries of the tumor.

2. The method of claim 1, wherein the marker is introduced by intravenous injection, by intratumoral injection, by inhalation, or by oral administration.

3. The method of claim 1, wherein the tumor is completely resected when the concentration of the marker in the cautery smoke corresponds to the concentration of the marker in normal tissue.

4. The method of claim 1, wherein the tumor marker comprises a perfluorinated alkane.

5. The method of claim 4, wherein the perfluorinated alkane comprises at least one of perfluoroethane, perfluoropropane, perfluoro-isopropane, perfluorobutane, perfluoro-isobutane, perfluoro-tertiarybutane, perfluoropentane, perfluoro-isopentane, perfluorohexane, perfluorooctyl bromide, or perfluoro-neopentane.

6. The method of claim 1, wherein the tumor marker is encapsulated in a plurality of microbubbles, wherein the microbubbles comprise a thermally degradable polymer.

7. The method of claim 6, wherein the thermally degradable polymer comprises at least one of methylcyanoacrylate, methoxyethyl cyanoacrylate, polymethacrylic acid, or polyethylene glycol.

8. The method of claim 1, wherein the tumor tissue comprises liver tissue.

9. The method of claim 1, wherein the tumor marker is a tumor-specific antibody, a fluorescently labeled antibody, a radioactive antibody, or an antibody specific for hepatocellular carcinoma.

10. The method of claim 1 further comprising waiting for a sufficient period between introducing and contacting, to allow the tumor marker to bind to tumor tissue.

11. The method of claim 1 further comprising administering one or more agents that enhance the selective binding of the tumor marker to the tumor tissue, the agent comprising a tumor selective peptide, a cell penetrating peptide, or a chemical substance.

12. The method of claim 11, wherein the tumor marker is a chemical substance.

13. The method of claim 12, wherein the chemical substance is a microbubble of perfluorobutane.

14. The method of claim 12, wherein the chemical substance is transported to the tumor tissue by active transport or passive transport.

15. The method of claim 12, wherein the chemical substance is transported to the tumor tissue by active transport and accumulates within the vicinity of the tumor tissue.

* * * * *

UNITED STATES PATENT AND TRADEMARK OFFICE
CERTIFICATE OF CORRECTION

PATENT NO. : 9,255,907 B2  
APPLICATION NO. : 14/363049  
DATED : February 9, 2016  
INVENTOR(S) : Heanue et al.

Page 1 of 1

It is certified that error appears in the above-identified patent and that said Letters Patent is hereby corrected as shown below:

In The Specification

In Column 1, Line 6, delete "§371" and insert -- § 371 --, therefor.

In Column 1, Line 21, delete "relics" and insert -- relies --, therefor.

In Column 3, Line 3, delete "Tf" and insert -- If --, therefor.

In Column 7, Line 22, delete "nanoparticic," and insert -- nanoparticles, --, therefor.

In Column 10, Line 5, delete "knife Both" and insert -- knife. Both --, therefor.

In The Claims

In Column 15, Line 39, in Claim 1, delete "resections;" and insert -- resection; --, therefor.

Signed and Sealed this
Fourteenth Day of June, 2016

Michelle K. Lee
*Director of the United States Patent and Trademark Office*